(12) United States Patent
Zaharchuk et al.

(10) Patent No.: US 11,361,431 B2
(45) Date of Patent: Jun. 14, 2022

(54) DOSE REDUCTION FOR MEDICAL IMAGING USING DEEP CONVOLUTIONAL NEURAL NETWORKS

(71) Applicant: The Board of Trustees of the Leland Stanford Junior University, Stanford, CA (US)

(72) Inventors: Greg Zaharchuk, Stanford, CA (US); John M. Pauly, Stanford, CA (US); Enhao Gong, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 270 days.

(21) Appl. No.: 16/615,227

(22) PCT Filed: Apr. 24, 2018

(86) PCT No.: PCT/US2018/029103
§ 371 (c)(1),
(2) Date: Nov. 20, 2019

(87) PCT Pub. No.: WO2018/200493
PCT Pub. Date: Nov. 1, 2018

(65) Prior Publication Data
US 2020/0311914 A1 Oct. 1, 2020

Related U.S. Application Data

(60) Provisional application No. 62/489,518, filed on Apr. 25, 2017.

(51) Int. Cl.
*G06K 9/00* (2022.01)
*G06T 7/00* (2017.01)
(Continued)

(52) U.S. Cl.
CPC ........... *G06T 7/0012* (2013.01); *G06N 20/10* (2019.01); *G06T 3/4007* (2013.01);
(Continued)

(58) Field of Classification Search
CPC . G06T 2207/20084; G06T 2207/20081; G06T 7/0012; G06T 2207/10081;
(Continued)

(56) References Cited

U.S. PATENT DOCUMENTS 10,970,887 B2 4/2021 Wang
2018/0144214 A1* 5/2018 Hsieh ..................... G06K 9/036

FOREIGN PATENT DOCUMENTS

EP 1387317 2/2004

OTHER PUBLICATIONS

Inception-V4, Inception-ResNetand the Impact of Residual Connections on Learning, Christian Szegedy, Sergey Ioffe, Vincent Vanhoucke, arXiv, 2016.*
(Continued)

*Primary Examiner* — Alex Kok S Liew
(74) *Attorney, Agent, or Firm* — Lumen Patent Firm

(57) ABSTRACT

A method of reducing radiation dose for radiology imaging modalities and nuclear medicine by using a convolutional network to generate a standard-dose nuclear medicine image from low-dose nuclear medicine image, where the network includes N convolution neural network (CNN) stages, where each stage includes M convolution layers having K×K kernels, where the network further includes an encoder-decoder structure having symmetry concatenate connections between corresponding stages, downsampling using pooling and upsampling using bilinear interpolation between the stages, where the network extracts multi-scale and high-level features from the low-dose image to simulate a high-dose image, and adding concatenate connections to the
(Continued)

low-dose image to preserve local information and resolution of the high-dose image, the high-dose image includes a dose reduction factor (DRF) equal to 1 of a radio tracer in a patient, the low-dose PET image includes a DRF of at least 4 of the radio tracer in the patient.

10 Claims, 17 Drawing Sheets

(51) Int. Cl.

| | | |
|---|---|---|
| *G16H 20/40* | (2018.01) | |
| *G16H 50/50* | (2018.01) | |
| *G16H 30/40* | (2018.01) | |
| *G06N 20/10* | (2019.01) | |
| *G06T 3/40* | (2006.01) | |
| *G06V 10/44* | (2022.01) | |

(52) U.S. Cl.
CPC .......... *G06V 10/454* (2022.01); *G16H 20/40* (2018.01); *G16H 30/40* (2018.01); *G16H 50/50* (2018.01); *G06T 2207/10081* (2013.01); *G06T 2207/10104* (2013.01); *G06T 2207/10108* (2013.01); *G06T 2207/20004* (2013.01); *G06T 2207/20084* (2013.01); *G06T 2207/30004* (2013.01); *G06V 2201/031* (2022.01)

(58) Field of Classification Search
CPC ............ G06T 2207/10088; G06T 7/11; G06T 2207/30096; G06T 11/006; G06T 2207/10104; G06T 2207/30004; G06T 2210/41; G06T 11/008; G06T 5/001; G06T 15/08; G06T 11/005; G06T 2207/10072; G06T 2207/10108; G06T 2207/10132; G06T 2207/30081; G06T 3/4007; G06N 3/0454; G06N 3/08; G06N 3/084; G06N 20/20; G06N 3/0445; G06N 3/0472; G06N 3/0481; G06N 3/082; G06N 3/088; G06N 20/00; G06N 20/10; G06N 3/04; G06N 3/02; G06N 7/005; G06N 10/00; G06N 3/063; G06N 5/003; G06N 5/025; G06N 7/00

See application file for complete search history.

(56) References Cited

OTHER PUBLICATIONS

Hashimoto, Deep learning-based attenuation correction for brain PET with various radiotracers, Apr. 2022, Sprinker (Year: 2022).*
Xu, et al., 200x Low-dose PET Reconstruction using Deep Learning, arXiv:1712.04119 [cs.CV], Dec. 12, 2017.
Hu Chen et al., "Low-Dose CT with a Residual Encoder-Decoder Convolutional Neural Network (RED-CNN)", Feb. 1, 2017, arXiv:1702.00288v1 [physics.med-ph].

* cited by examiner

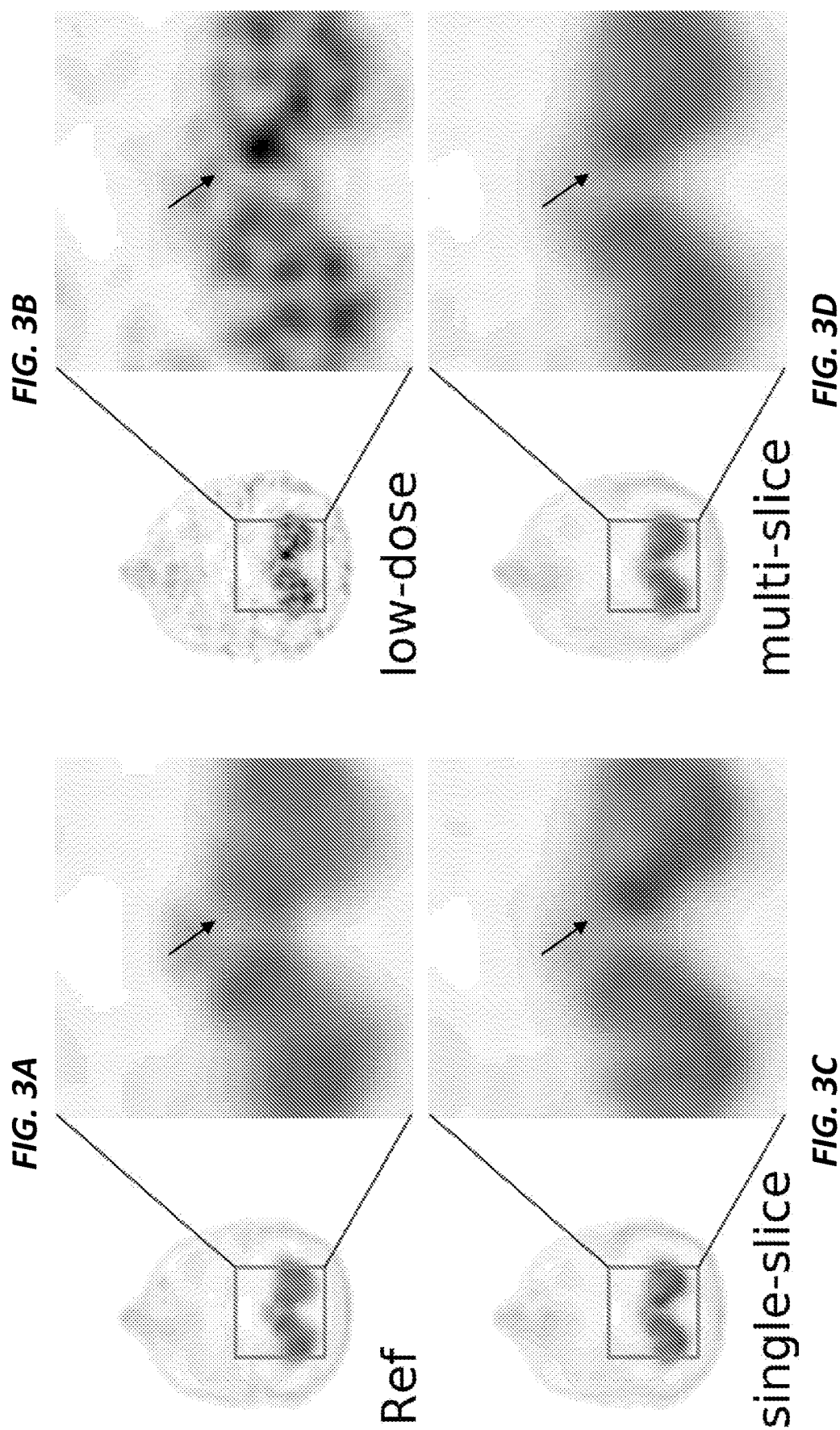

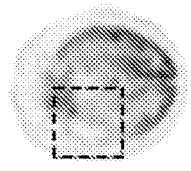 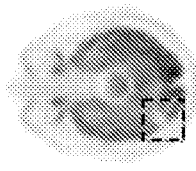
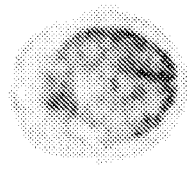 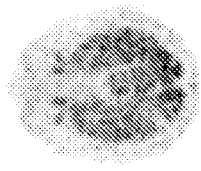
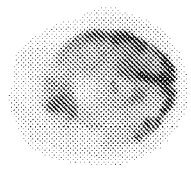 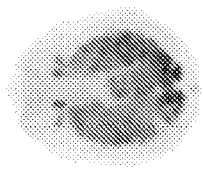
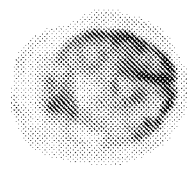 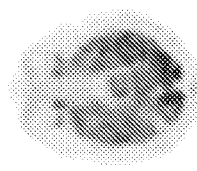
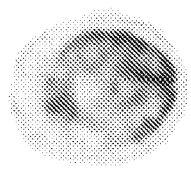 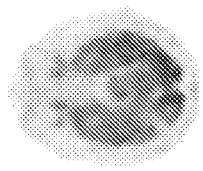
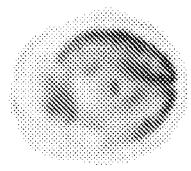 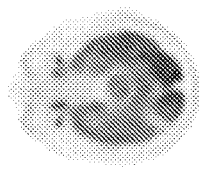
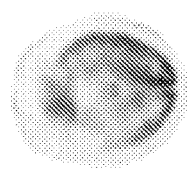 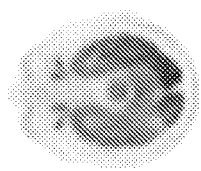
FIG. 6A  FIG. 6B  FIG. 6C  FIG. 6D  FIG. 6E  FIG. 6F  FIG. 6G

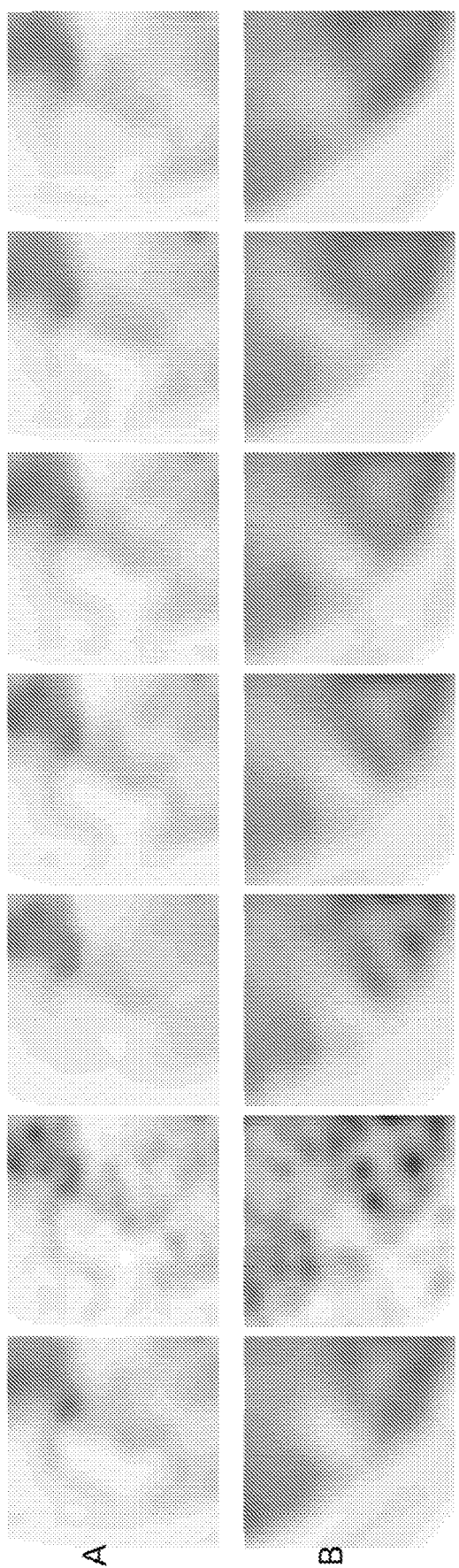

DOSE REDUCTION FOR MEDICAL IMAGING USING DEEP CONVOLUTIONAL NEURAL NETWORKS

FIELD OF THE INVENTION

This invention relates generally to medical imaging. More particularly, the invention relates to medical imaging technology with the purpose of dose reduction to lower risk to patients.

BACKGROUND OF THE INVENTION

Positron emission tomography (PET) has a wide range of clinical applications, such as cancer diagnosis, tumor detection and early diagnosis of neuro diseases, for its ability of cellular-level imaging and high specificity. In order to acquire a high quality PET image for diagnostic purposes, a standard dose of radioactive tracer should be injected to the subject, which will lead to higher risk of damage by radiation exposure. Usually, a PET scan or a scan of PET/MR and PET/CT can expose patients with even more ionizing radiation than a scan using CT alone. To minimize such risk, the well-known principle of ALARA (as low as reasonably achievable) is adopted in clinical practice.

To address this problem, many algorithms were proposed to improve the image quality for a low-dose PET image. In general, these algorithms can be categorized into three categories: (1) iterative reconstruction algorithm, (2) image filtering and post-processing, and (3) machine learning.

Iterative reconstruction algorithms formulated the low-dose reconstruction problem as a convex optimization problem combining a statistical model of the acquired data (i.e., sinogram or listmode) and the regularization term to suppress noise. Previously proposed is an iterative algorithm using a Total Variation (TV) regularization to reduce the noise of synthetic emission phantom with different photon counts. Although iterative reconstruction algorithms are potentially the most accurate since they consider the raw count information directly, they also have three main weaknesses. First, the substantial computational expenses from interacting with all the acquired data make most of these kind of methods time consuming. Second, iterative methods are typically vendor-specific, since different scanners may adopt different geometric configurations, data formats (e.g., time-of-flight (TOF) and depth-of-interaction (DOI)), and data correction procedures, which will significantly affect the raw data. Finally, in these methods, a predefined regularization term is need, which may lead to undesirable over-smoothing, artifacts or hallucinated textures.

As for image processing methods, several general-purpose image denoising algorithms, such as nonlocal means (NLM) and block-matching 3D (BM3D), are introduced into PET image denoising. In addition, one attempt combined a singular value thresholding method and an unbiased risk estimate to denoise PET image. Based on the multi-scale Curvelet and Wavelet analysis, one group proposed a method to denoise PET image while preserving image resolution and quantification.

Another important category is the data-driven machine learning methods such as mapping-based sparse representation, semi-supervised tripled dictionary, and multilevel canonical correlation analysis. Instead of denoising the low-dose PET image directly, machine learning methods utilize paired low-dose and standard-dose images to train models that can predict standard-dose images from low-dose inputs.

Recently, deep learning attracted a lot of attention in computer vision applications, yielding much better results compared with traditional methods, and achieves human-level performance in some tasks such as image classification and face verification. Several key factors contribute to the success of deep learning methods: (1) acceleration of parallel computation due to modern powerful GPUs that make it possible to train models with large amounts of parameters, (2) larger datasets are released, boosting more open source research and training, e.g., ImageNet, and (3) new efficient neural network structures, e.g., convolution neural network (CNN) which utilizes weight sharing and local connection. In addition, deep learning methods are also successfully applied to the category of low-level vision problems including image denoising, super resolution, and image restoration, etc., achieving state-of-the art results.

Although these methods mainly focus on natural image processing, several efforts have been made to apply these promising methods to medical image analysis. U-Net is a fully convolutional network for medical image segmentation. which comprises a contracting path and an expansive path to extract features at different resolution. To regain the lost resolution information, U-Net also employs skip connection to concatenate corresponding contracting and expansive steps. Inspired by U-Net, one group proposed a multi-scale CNN to remove streaking artifacts in sparse-view CT images, using residual learning. WaveNet, which is also used for low-dose X-ray CT reconstruction, adopts a similar structure combined with multi-scale wavelet transformation as feature augmentation for input data. In the field of low-dose PET reconstruction, compared with low-dose CT reconstruction, there are few researches on low-dose PET image denoising that utilize deep learning methods. Another group proposed a deep learning method to predict standard-dose PET images from low-dose PET images and corresponding MR T1 images with an auto-context convolution network, which tries to refine the prediction results step by step.

Recent development in simultaneous PET/MRI systems make it possible to utilize extra information from MRI to improve image quality in PET correction, including attenuation correction, motion correction and partial volume correction. Besides, multi-contrast MRI, including structural T1 image and DTI related contrasts are shown to be beneficial to low-dose PET reconstruction.

Regarding a dose reduction factor (DRF), conventional methods have been used for denoising standard-dose images (DRF=1) while other conventional methods have been used to try to reconstruct standard-dose images from quarter-dose images (DRF=4).

What is needed is a deep learning method to reconstruct standard-dose PET images from ultra-low-dose images.

SUMMARY OF THE INVENTION

To address the needs in the art, a method of reducing radiation dose for radiology imaging modalities and nuclear medicine applications is provided that includes using a convolutional network to generate a standard-dose nuclear medicine image from low-dose nuclear medicine image, where the convolutional network includes N convolution neural network (CNN) stages, where each CNN stage includes M convolution layers having K×K kernels, where the convolutional network further includes an encoder-decoder structure having symmetry concatenate connections between corresponding CNN stages, downsampling using pooling and upsampling using bilinear interpolation between the stages, where the network extracts multi-scale and high-level features from the low-dose image to simulate a high-dose image, and adding concatenate connections to the low-dose image to preserve local information and resolution of the high-dose image, where the high-dose image includes a dose reduction factor (DRF) equal to 1 of a radio tracer in a patient, where the low-dose PET image includes a DRF equal to at least 4 of the radio tracer in the patient.

According to one aspect of the invention, the DRF is in a range of 4 to 200.

In another aspect of the invention, the standard-dose nuclear medicine image is generated from the low-dose nuclear medicine image and corresponding multi-contrast MR images as multi-modality inputs.

In a further aspect of the invention, the nuclear medicine image is generated using methods that include CT, PET, PET/CT, PET/MR, SPECT, or other nuclear medicine imaging methods.

According to one aspect of the invention, a signal-to-noise-ratio (SNR) in the low-dose nuclear medicine image is increased using an encoder-decoder residual deep network with concatenate skip connections, where the skip connections include a residual connection from an input image to an output image of the method, or concatenating connections between corresponding encoder and decoder layers.

In yet another aspect of the invention, the low-dose nuclear medicine image further includes a combination of multiple slices and multiple contrast images as input. Here, the combination of the multiple slices and the multiple contrast images can include T1w MR images, T2w MR images, FLAIR MR images, Diffusion MR images, Perfusion MRI images, susceptibility MR images, MR based Attenuation Correction Maps, MR water-fat images, CT images, or CT based Attenuation Correction Maps, where the Perfusion MRI images comprise Arterial Spin Labeling sequences.

In another aspect of the invention the method further includes an algorithm to determine how many input slices and which input contrasts are contributing the most to the method, where the algorithm adaptively decides how many input slices and input contrasts to use.

According to another aspect of the invention, mixed cost functions can include L1/Mean-absolute-error, structural similarity loss, or adaptive trained loss are used, where the adaptive trained loss comprises generative adversarial network loss and perceptual loss function using network models.

According to one embodiment, the invention includes a system of generating high-quality images for radiology imaging modalities and nuclear medicine applications from low-radiation-dose samples that includes using a medical imager for taking multiple slices of low-radiation-dose images, or low-radiation-dose images and multi-contrast images acquired together, as a stacking of multiple 2 dimensional images or 3 dimensional images as a system input, applying a deep network-based regression task to the input images, where the deep network-based regression task includes N convolution neural network (CNN) stages, where each the CNN stage comprises M convolution layers having K×K kernels, where the CNN includes an encoder-decoder structure having symmetry concatenate connections between corresponding the CNN stages, an encoder-decoder residual deep network with concatenate skip connections, where the skip connections include a residual connection from an input image to an output image, outputting radiology or nuclear medicine images having an image quality as a standard-radiation-dose image, where the image quality includes a resolution, a contrast, and a signal-to-noise-ratio that are improved from low-radiation-dose inputs.

BRIEF DESCRIPTION OF THE DRAWINGS

FIGS. 3A-3D show the effect of multi-slice input using (3A) standard-dose, (3B) 200× low-dose, (3C) reconstructed result using single-slice input, and (3D) reconstructed result using multi-slice input (3 slices), according to the current invention.

FIGS. 6A-6G show results from different methods for comparison, (6A) standard-dose, (6B) low-dose, (6C) NLM, (6D) BM3D, (6E) AC-Net, (6F) ResUNet and (6G) ResUNet+MR.

FIGS. 7A-7G show the zoomed part of FIGS. 6A-6G, where shown is (7A) standard-dose, (7B) low-dose, (7C) NLM, (7D) BM3D, (7E) AC-Net, (7F) ResUNet and (7G) ResUNet+MR.

DETAILED DESCRIPTION

Figure 1A:
FIG. 1 shows PET images with normal dose and different levels of dose reduction, (1A) standard-dose, (1B) quarter-dose, (1C) twentieth-dose, and (1D) two-hundredth-dose, according to the current invention.
Figure 1B:
Figure 1C:
Figure 1D:

Positron emission tomography (PET) is widely used in various clinical applications, including cancer diagnosis, heart disease and neuro disorders. The use of radioactive tracer in PET imaging raises concerns due to the risk of radiation exposure. To minimize this potential risk in PET imaging, efforts have been made to reduce the amount of radiotracer usage. However, lowing dose results in low Signal-to-Noise-Ratio (SNR) and loss of information, both of which will heavily affect clinical diagnosis. As well, ill-conditioning of low-dose PET image reconstruction makes it a difficult problem for iterative reconstruction algorithms. Previous methods proposed are typically complicated and slow, yet still cannot yield satisfactory results at significantly low dose. The current invention provides a deep learning method to resolve this issue with an encoder-decoder residual deep network with concatenate skip connections. Experiments show the current invention reconstructs low-dose PET images to a standard-dose quality with only two-hundredths of the dose. Different cost functions for training model are disclosed. A multi-slice input embodiment is described to provide the network with more structural information and make it more robust to noise. A multi-contrast MRI acquired from simultaneous PET/MRI is also provided to the network to improve its performance. Evaluation on ultra-low-dose clinical data shows that the current invention achieves better results than the state-of-the-art methods and reconstructs images with comparable quality using only 0.5% of the original regular dose.

According to the current invention, multi-contrast MRI is adopted to improve the performance of one aspect of the invention's model. A deep learning method is used to reconstruct standard-dose PET images from ultra-low-dose images (99.5% reduction or DRF=200), using a fully convolutional encoder-decoder residual deep network model. This is advantageous for enabling ultra-low-dose PET reconstruction at a high reduction factor and with in-vivo PET datasets.

To further describe example dataset and experiments are disclosed that setup PET/MRI images from eight patients with glioblastoma (GBM), which were acquired on a simultaneous time-of-flight enabled PET/MRI system (SIGNA, GE Healthcare) with standard dose of 18F-fluorodeoxyglucose (FDG) (370 MBq). Images were acquired for about 40 min, beginning 45 min after injection. The raw count list-mode datasets were stored for each scan and then generate synthesized low-dose raw data at DRF=200 by simply randomly selecting 0:5% of the count events, spread uniformly over the entire acquisition period. Then PET images were reconstructed from the acquired data at DRF=1 (standard full dose) and DRF=200 (target low dose) using standard OSEM methods (28 subsets, 2 iterations). Note, the system according to the current invention beyond 4× reduction to 10×, 100×-200× reduction or even completely remove radiation and generate zero-dose image from MRIs.

Each patient underwent three independent scans. The size of each reconstructed 3D PET data is 25625689. There are slices of air at the top and bottom, which are removed. To avoid over fitting, data augmentation is adopted during the training process to simulate a larger dataset. Before being fed into the network, the images are randomly flipped along x and y axes and transposed.

For the deep learning based low-dose PET reconstruction, the current invention is provided to train a model to learn to reconstruct from the DRF=200 image to DRF=1 reconstruction.

Figure 2A:
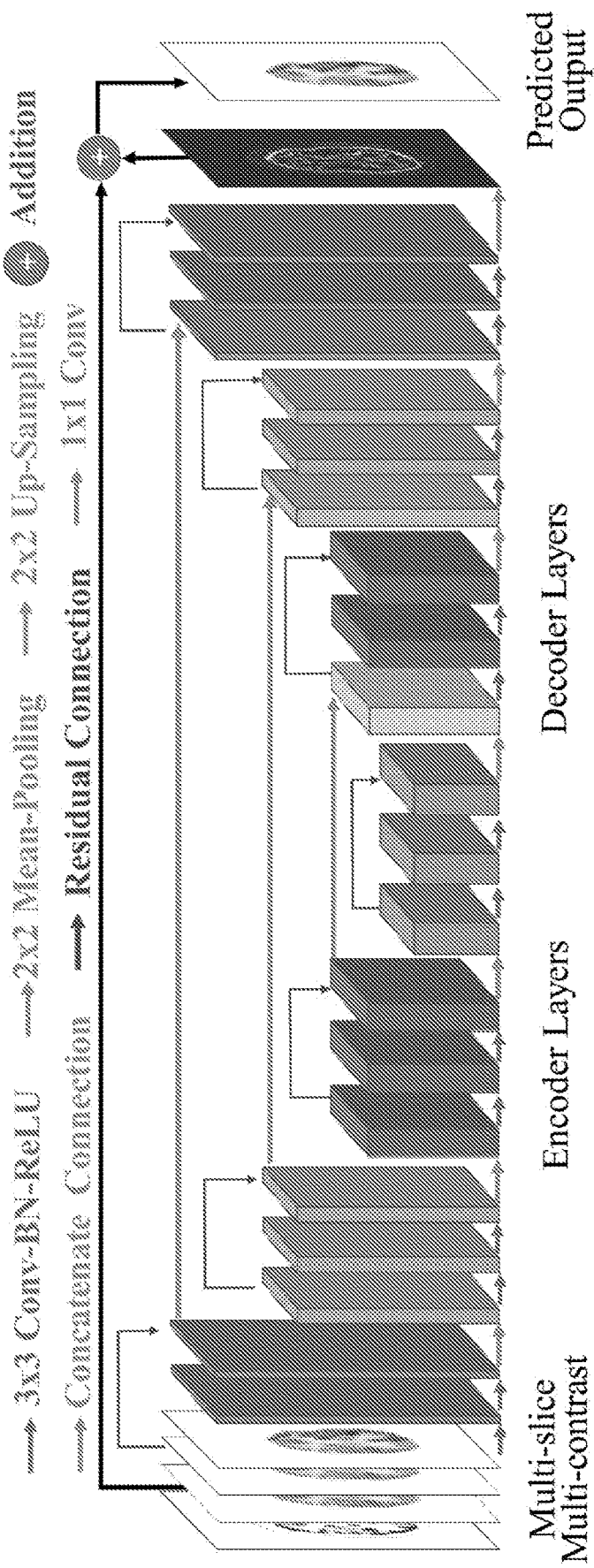
FIGS. 2A-2B show the overall architectures of network method and system architecture work flow for low-dose PET reconstruction using deep learning, according to the current invention.

FIG. 2A shows one embodiment of a fully convolutional network that is based on an encoder-decoder structure with symmetry concatenate connections between corresponding stages. The provided network structure is distinct from the UNet structure by using modification for image synthesis task instead of segmentation task. Specifically, each stage is a residual block that includes convolution with 3×3 kernels, batch normalization, and rectified linear unit (ReLU). The downsampling and upsampling between stages are done by 2×2 max pooling and bilinear interpolation respectively. By downsampling and then upsampling the image, the network can extract the multi-scale and high-level features from the image. The low-dose PET image reconstruction task is similar to image denoising, which is within the category of low-level vision problems and are susceptible to resolution loss if only an encoding-decoding procedure is used. Therefore, concatenate connections are added to preserve local information and resolution of the image.

Figure 2B:
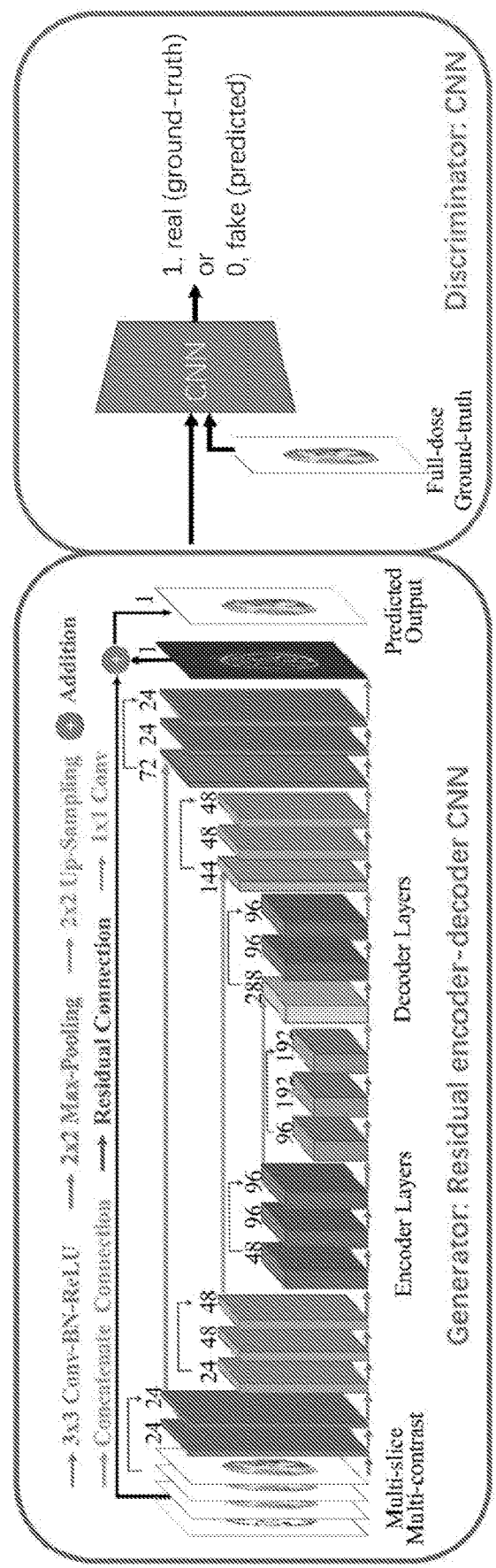

FIG. 2B shows a deep network that is trained to generate standard-dose PET image, from low-dose PET image and corresponding multi-contrast MR images as multi-modality inputs. As shown, there are N CNN stages and each stage is a block that includes an M convolution layer with K×K kernels. The results are shown for settings with N=7, M=2, K=3. By downsampling and then upsampling the image, the network can extract the multi-scale and high-level features from the image. Symmetric concatenate connections are used to preserve high-resolution information and improve the network performance.

Residual learning was first introduced into CNN as a technique to avoid performance degradation when training very deep CNNs. It shows by separating the identity and the residual part, the neural network can be trained more effectively and efficiently. Originally, residual learning is used in image recognition task and later proposed was DnCNN, which is the first denoising convolution network using residual learning. It was shown that using persistent homology analysis, the residual manifold of CT artifacts has a much simpler structure. The network of the current invention employs the residual learning technique, by adding a residual connection from input to output directly, i.e., instead of learning to generate standard-dose PET images directly, the network tries to learn the difference between standard-dose images outputs and low-dose images inputs. One aspect of the invention shows that residual learning can also lead to a significant improvement in network performance for low-dose PET reconstruction problem.

In some embodiments of the invention, multi-slice may be used as input to the system. This is beneficial because using only the low-dose image as input for the neural network may not provide enough information to reconstruct the standard-dose counterpart. As shown in FIG. 1, the noise due to dose reduction cannot be fully eliminated by the network for the network may have insufficient information to distinguish noise from brain structure. To address this problem, multi-slice input is used instead of single-slice input, i.e., adjoining slices are stacked as different input channels. In general, the multi-slice inputs can be regarded as a kind of feature augmentation. Since the structure of the brain is deterministic, adjoining slices may share similar structure while having different noise which, is random. Thus, combining different slices as input can provide the network with 2.5D structural information that can be used to distinguish random noise from the consistent structure. Any number of adjoining slices may be used. For example, at least two, three, four, five, six, seven, eight, nine, ten, or more adjoining slices may be utilized as input. One example is illustrated in FIG. 3, in the low-dose PET image there is a black noise in the zoomed part, which cannot be eliminated but hallucinated as a structure by the network trained with single-slice input. However, the network trained with three-slice input can achieve better results, as shown in FIG. 3(D). Training 2.5D multi-slice inputs is different from training with 3D convolution network since the former solution sues depth-wise operation of 3D convolution which has fewer parameters and higher efficiency.

For using multi-contrast MRI, two different MR contrasts, T1 and FLAIR are used in one embodiment of the invention. Although simultaneously acquired PET and MR images lie in the same coordinate system, they may have different resolutions.

To address this problem, MR images are registered to the corresponding PET image using affine registration. Multi-contrast MRI is concatenated with multi-slice input described below along the channel axis. The multi-contrast image includes but is not limited to: T1w MR images, T2w MR images, FLAIR MR images, Diffusion MR images, Perfusion MRI images (such as Arterial Spin Labeling sequences), Susceptibility MR images, MR based Attenuation Correction Maps, MR water-fat images, CT images and CT based Attenuation Correction Maps.

Regarding the selection of loss functions, the mean squared error (MSE) or L2 loss is still the most popular choice of loss function in training networks for image restoration problems, e.g., super resolution or denoising. The use of MSE as a loss function is under the assumption of additive white Gaussian noise, which should be independent of the local features of the image. However, this is not valid for low-dose PET reconstruction in general. Since the intensity of PET image reflects the activity distribution of a tracer in the subject, and the noise results from dose reduction as related to the counting of each detector, noise and spatial information are not independent. In addition, the MSE loss may be not suitable for task related to clinical evaluation for it relates poorly to the human visual system and produces splotchy artifacts.

Aside from the traditional MSE, there are other loss functions that can be used to measure image similarity between reconstructed image and the ground-truth image. The L1 loss is the mean absolute error of two images, which can be defined as $$L^{l_1} = \frac{1}{NM} \sum_{i=1}^{N} \sum_{j=1}^{M} |x_{ij} - y_{ij}| \quad (1)$$

where N, M are number of rows and columns of the image respectively, while $x_{ij}$ and $y_{ij}$ denote the intensity at pixel (i; j) in the two images. To measure the structural and perceptual similarity, structural similarity index (SSIM), and multi-scale the structural similarity index (MS-SSIM) are proposed and can be estimated as $$L^{SSIM} = \frac{1}{NM} \sum_{i=1}^{N} \sum_{j=1}^{M} (1 - SSIM(i, j)) \quad (2)$$

$$L^{MS\text{-}SSIM} = \frac{1}{NM} \sum_{i=1}^{N} \sum_{j=1}^{M} (1 - MS\text{-}SSIM(i, j)) \quad (3)$$

where $$SSIM(i, j) = \frac{(2\mu_x\mu_y + C_1)}{(\mu_x^2 + \mu_y^2 + C_1)} * \frac{(2\sigma_{xy} + C_2)}{(\sigma_x^2 + \sigma_y^2 + C_2)} \quad (4)$$
$$= l(i, j) * cs(i, j)$$

$$MS\text{-}SSIM(i, j) = l_K(i, j) * \prod_{k=1}^{K} cs_j(i, j) \quad (5)$$

C1 and C2 are constants. $\mu_x$, $\mu_y$, $\sigma_x$, $\sigma_y$, and $\sigma_{xy}$ are the image statistics calculated in the patch centered at pixel (i; j). K is the number of level of multi-scale.

Recent researches have suggested that L1, SSIM, MSSIM are more perceptually preferable in image generative model. Among these three alternatives, the L1 loss can not only avoid the patchy artifact brought by L2 loss but add almost no overhead in back propagation compared with SSIM and MS-SSIM. Therefore, the L1 loss is selected as a loss function for training procedure in the following example experiments.

Regarding the computation environment and hardware settings, all the computation works were done on a Ubuntu server with 2 NVIDIA GTX 1080Ti GPUs. The network of the current invention is implemented in TensorFlow. The RMSprop optimizer is used in the experiments with a learning rate initialized by $1\times10^{-3}$, which slowly decreases down to $2{:}5\times10^{-4}$. The network was trained for 120 epochs. Convolution kernels were initialized with truncated Gaussian distributions with zero mean and standard deviation 0.02. All biases are initialized with zero.

To evaluate the performance of the method of the current invention and demonstrate its generalization for new datasets, especially for new patient data with a different pathology, the leave-one-out cross validation (LOOCV) was used. For each of the patient dataset, the full-dose reconstruction was generated using the model trained only on the other eight patients. The statistics of LOOCV results were used to quantify the generalization error of the model according to one embodiment of the invention. To quantitatively evaluate image quality, three similarity metrics are used in our experiment, including the normalized root mean square error (NRMSE), peak signal to noise ratio (PSNR) and SSIM. SSIM is defined in equation 4, while NRMSE and PSNR are defined as follows.

$$NRMSE = \sqrt{\frac{\sum_{i=1}^{N}\sum_{j=1}^{M}(x_{ij}-y_{ij})^2}{\sum_{i=1}^{N}\sum_{j=1}^{M}y_{ij}^2}} \quad (6)$$

$$PSNR = 20 * \log_{10}\left(\frac{MAX}{\sqrt{MSE}}\right) \quad (7)$$

where MAX is the is the peak intensity of the image. To better match the metric computation to the real clinical assessment, all the similarity metrics were computed after applying a brain mask estimated using image support.

Turning now to the results, starting with a comparison with other methods, method of the current invention was compared against three state-of-the-art denoising methods in low-dose PET reconstruction, including NLM, BM3D and auto-context network (AC-Net). Cross validation is conducted to evaluate these methods.

Figure 4A:
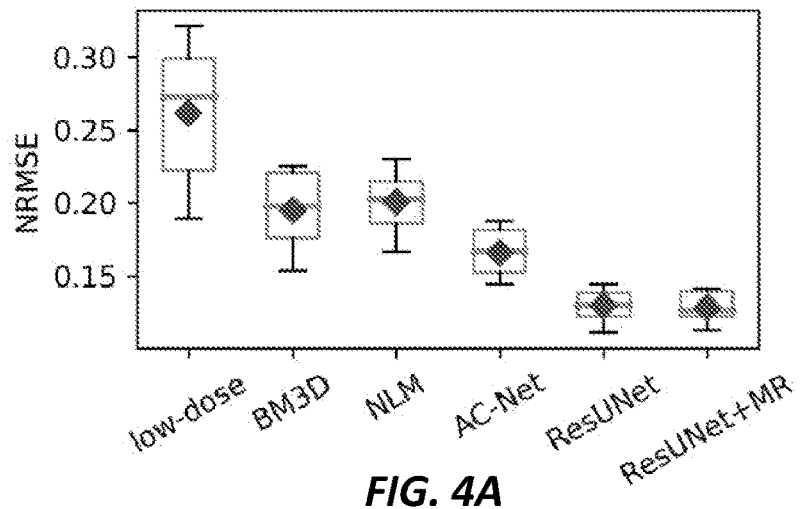
FIGS. 4A-4C show a comparison of the averaged performance and similarity metrics of different methods for low-dose reconstruction, where the diamonds denote means, according to the current invention.
Figure 4B:
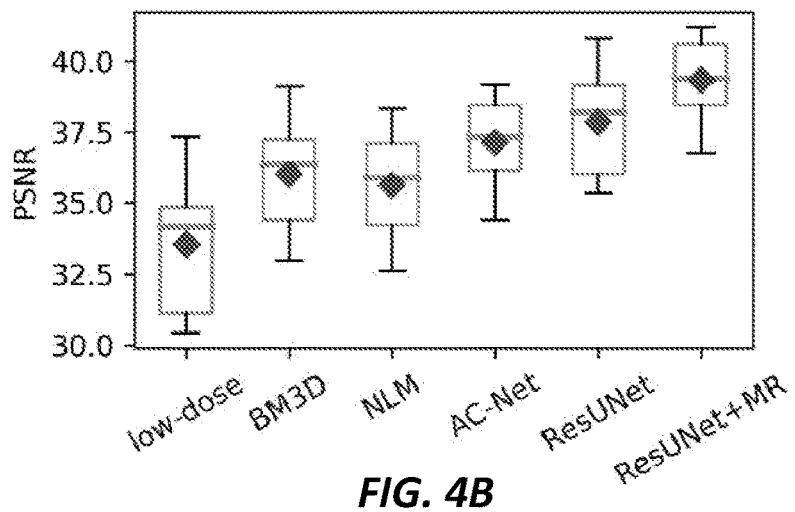
Figure 4C:
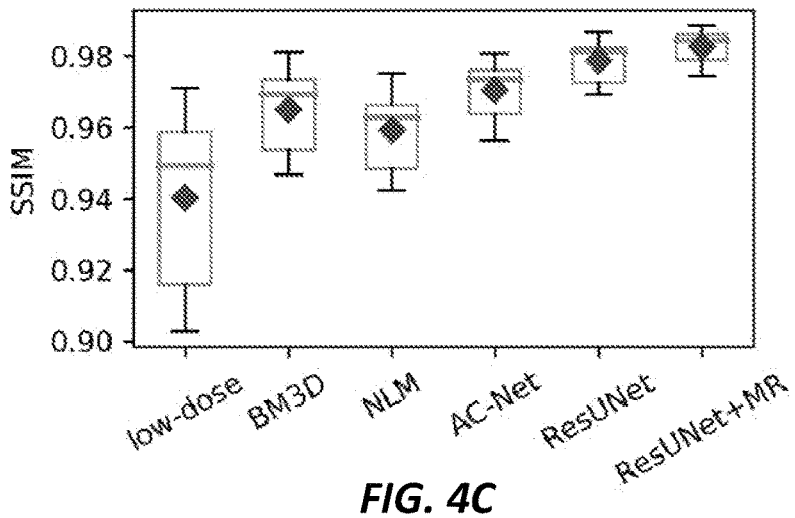
Figure 5A:
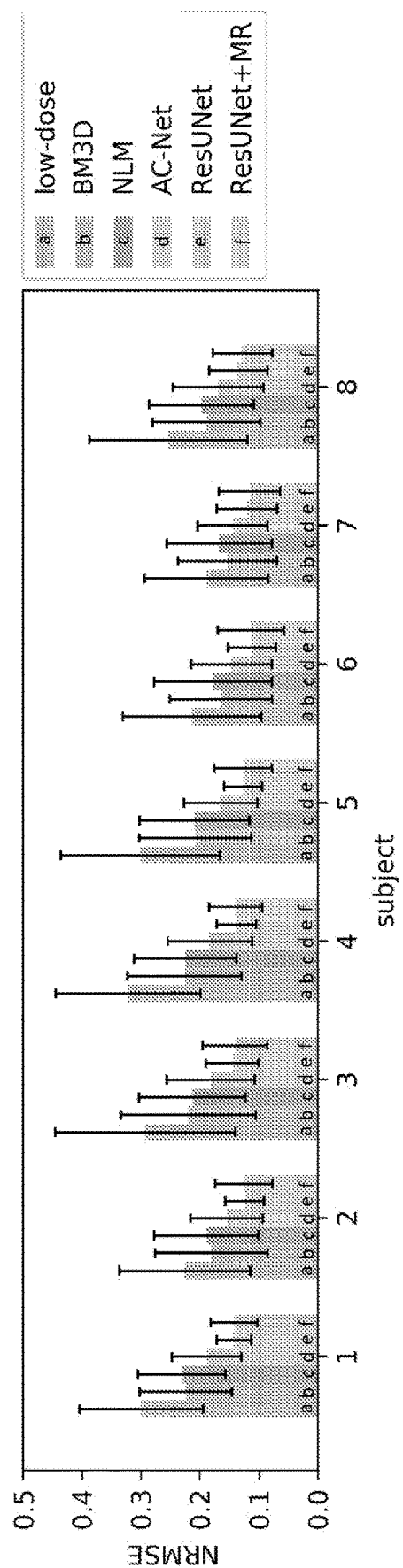
FIGS. 5A-5C show quantitative comparisons between the system and method of the current invention and previous methods using LOOCV.
Figure 5B:
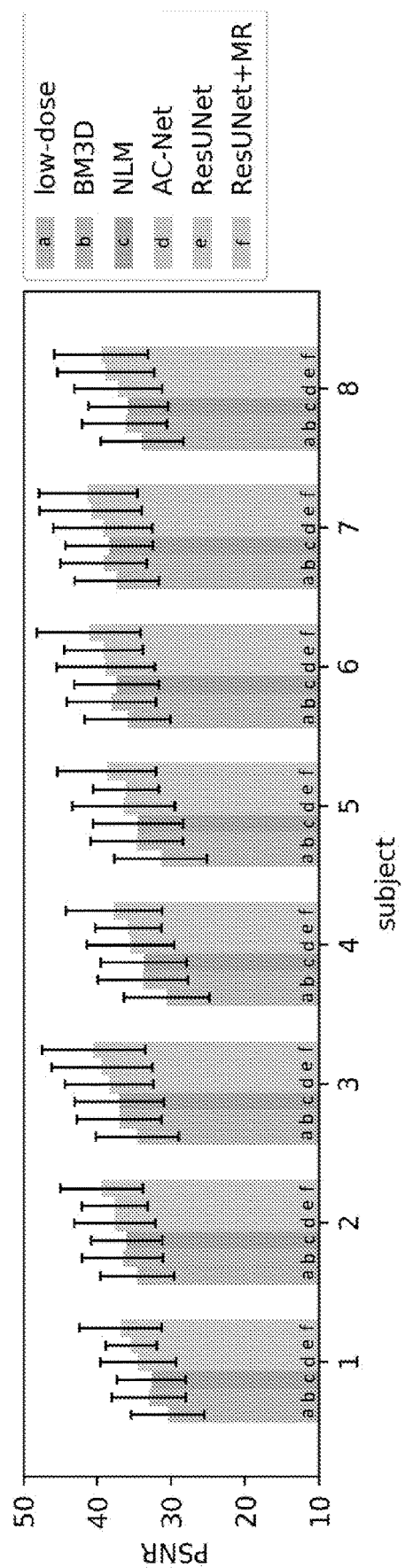
Figure 5C:
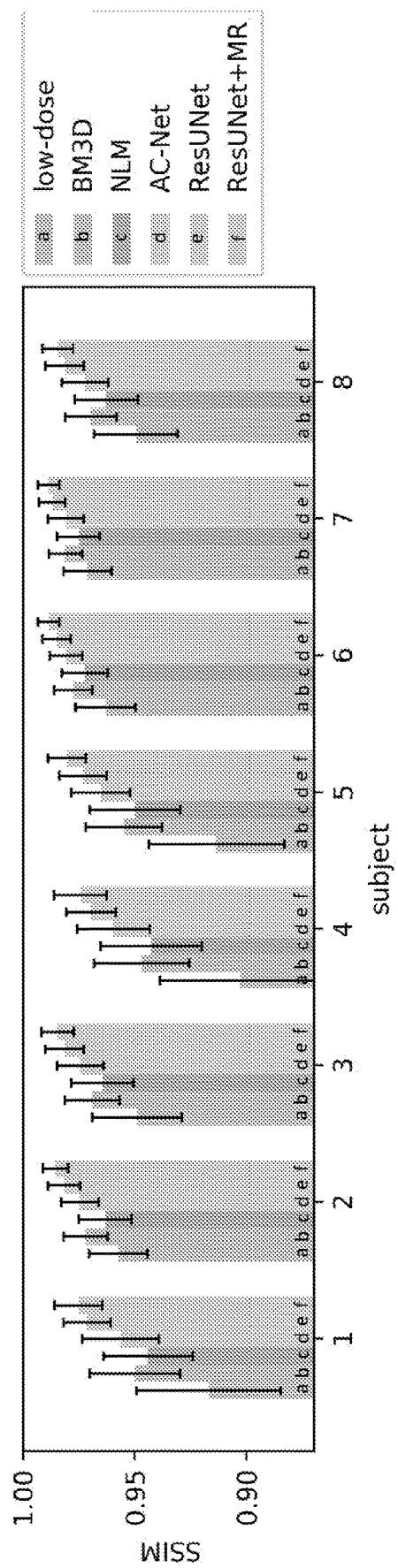

FIG. 4 shows the average performance in terms of NRMSE, PSNR and SSIM of all the subjects, while FIG. 5 gives the scores of these three metrics for all 9 subjects in the leave one-out testing.

To examine perceptual image quality, two representative slices are selected from different subjects. The quantitative metrics in terms of NRMSE, PSNR and SSIM of the selected slices are listed in Table I. The reconstruction results, zoomed tumors are visually illustrated in FIG. 6, and FIG. 7.

TABLE I

QUANTITATIVE RESULTS ASSOCIATED WITH DIFFERENT ALGORITHMS FOR REPRESENTAIVE SLICES.

|  | slice A | | | slice B | | |
|---|---|---|---|---|---|---|
|  | NRMSE | PSNR | SSIM | NRMSE | PSNR | SSIM |
| low-dose | 0.162 | 32.59 | 0.949 | 0.243 | 27.49 | 0.875 |
| NLM | 0.134 | 34.24 | 0.959 | 0.164 | 30.88 | 0.931 |
| BM3D | 0.123 | 34.99 | 0.970 | 0.150 | 31.66 | 0.941 |
| AC-Net | 0.119 | 35.23 | 0.971 | 0.136 | 32.50 | 0.951 |
| ResUNet | 0.116 | 35.46 | 0.975 | 0.118 | 33.76 | 0.964 |
| +MR | 0.113 | 35.69 | 0.978 | 0.106 | 34.69 | 0.972 |

Figure 8A:
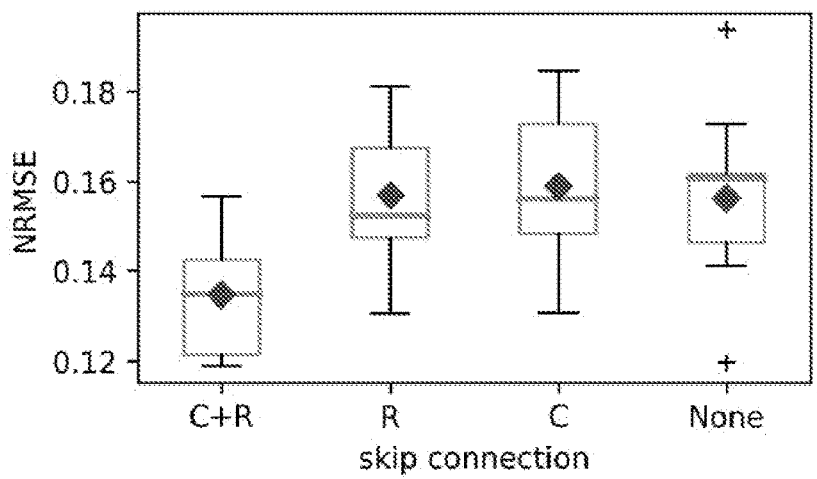
FIGS. 8A-8C show similarity metrics of network with different types of skip connection, where R means residual connection and C means concatenate connection, according to the current invention.
Figure 8B:
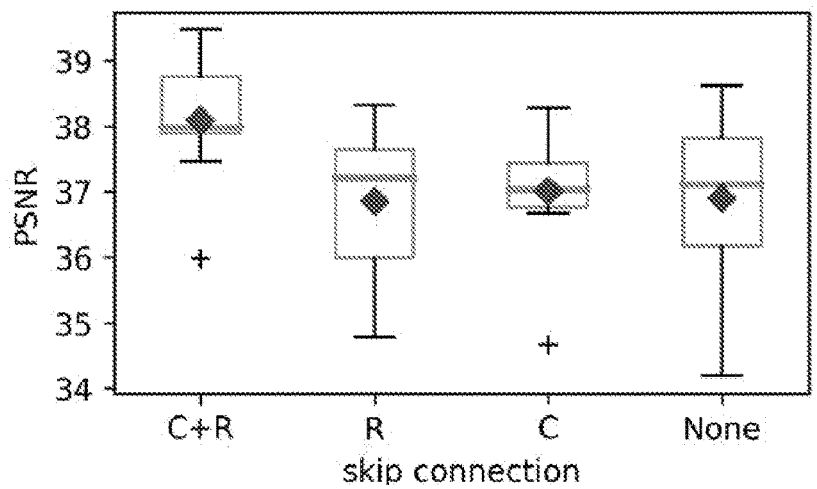
Figure 8C:
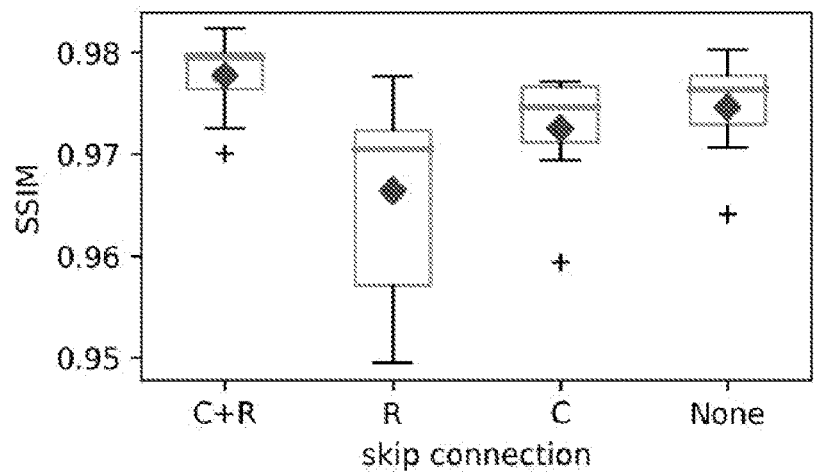

In some embodiments, the network may employ skip connection components. The network may utilize one or more skip connection components that may or may not be of the same type. For example, there may be two types of skip connections in the network. One is the residual connection from input to output, and the other is the concatenating connections between corresponding encoder and decoder layers. To evaluate the effect of these two types of skip connection on the network performance, four different models are trained and tested, i.e., (1) with both types of skip connection, (2) with only concatenate connection, (3) with only residual connection, and (4) without any skip connection. FIG. 7 shows the different testing loss of these four models during training and the quantitative results of cross validation are illustrated in FIG. 8.

As mentioned above, multi-slice input was used to combine information from adjoining slices so that the network can more accurately generate reconstruction with less noise and artifact while robustly preserve original structure and details.

To study the limit of this technique, networks with different numbers of input slices (1, 3, 5, 7) are trained and their results are compared, shown in FIGS. 9A-9F.

Figure 9A:
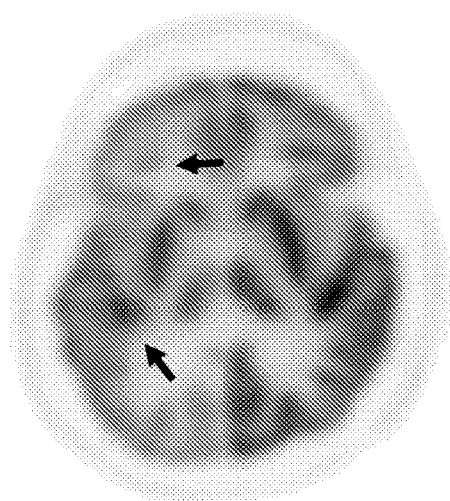
FIGS. 9A-9F show reference, inputs and reconstruction results using models with different settings in multi-slice inputs, where shown is (9A) standard-dose, (9B) low-dose, (9C) single slice, (9D) three slices, (9E) five slices, and (9F) seven slices, according to the current invention.
Figure 9B:
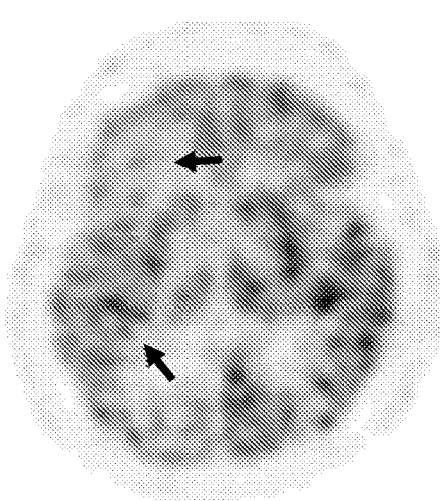
Figure 9C:
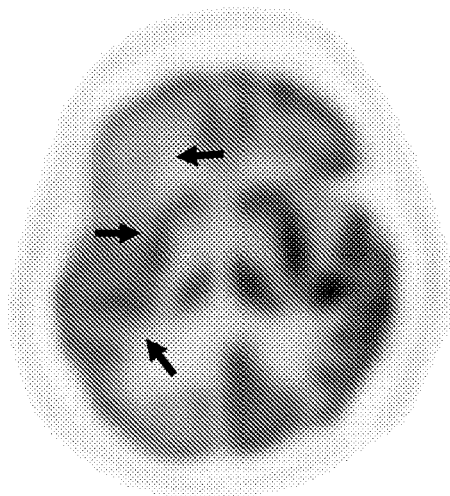
Figure 9D:
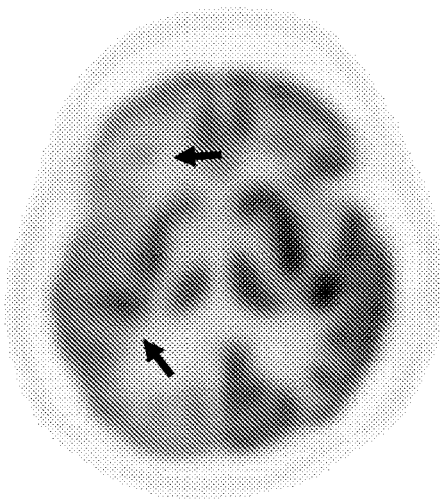
Figure 9E:
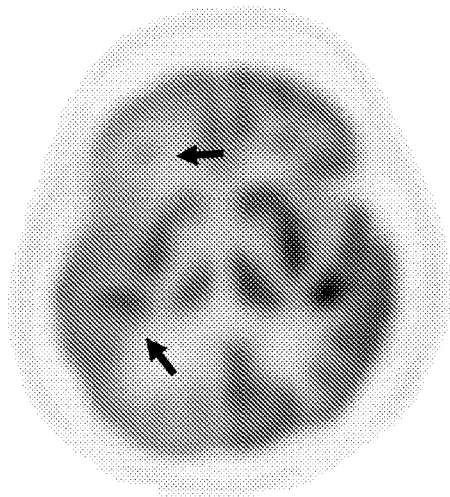
Figure 9F:
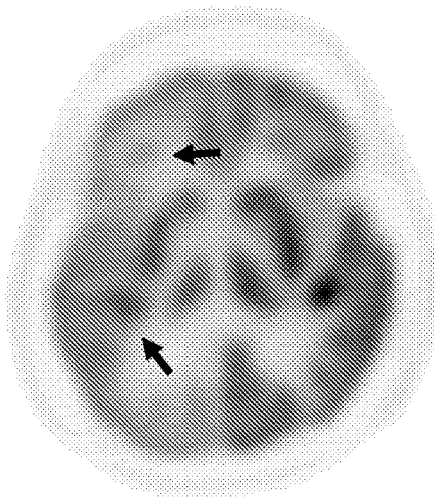
Figure 10A:
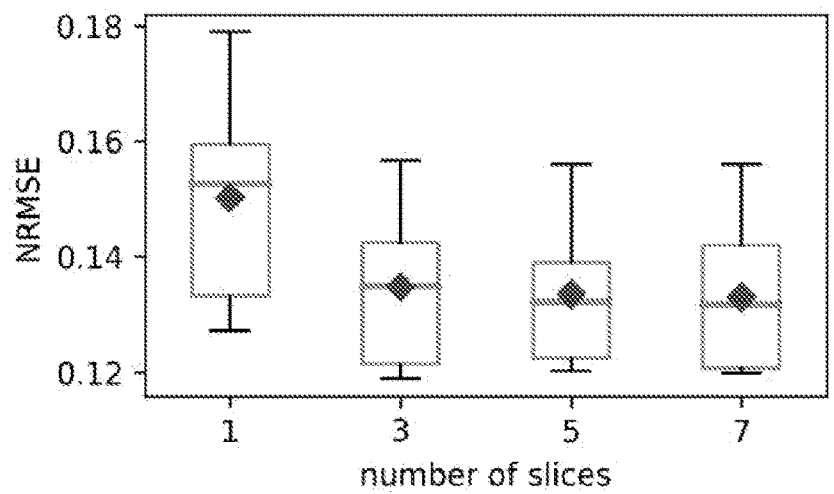
FIGS. 10A-10C show similarity metrics for networks trained with different numbers of input slices, according to the current invention.
Figure 10B:
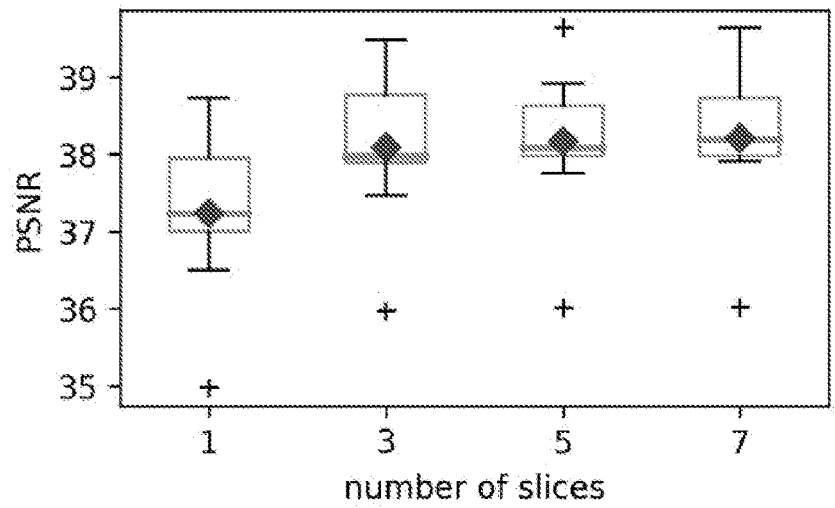
Figure 10C:
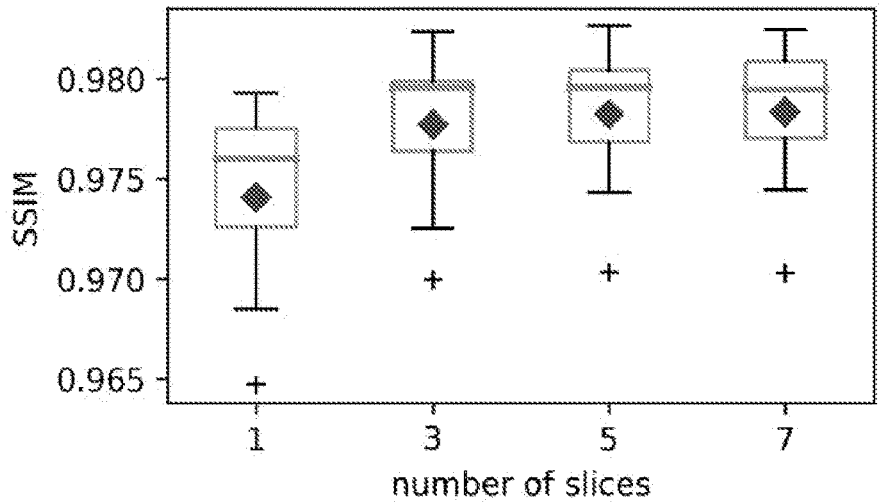

FIG. 10 shows results of three similarity metrics of networks trained with different numbers of slices as 2.5D inputs in the network. The evolutions of the three metrics all validate the performance gain of the method of the current invention using more input slice numbers. Compared with single-slice input, three-slice input can provide significantly better results. However, the performance gain of the network, by continuously adding slices more than 3 slices, is not as significant. Similar phenomenon can be seen in FIGS. 9A-9F. FIGS. 9D-9F contain details that are missing or blurred in FIG. 9C. However, FIGS. 9D-9F are perceptually similar.

Figure 11A:
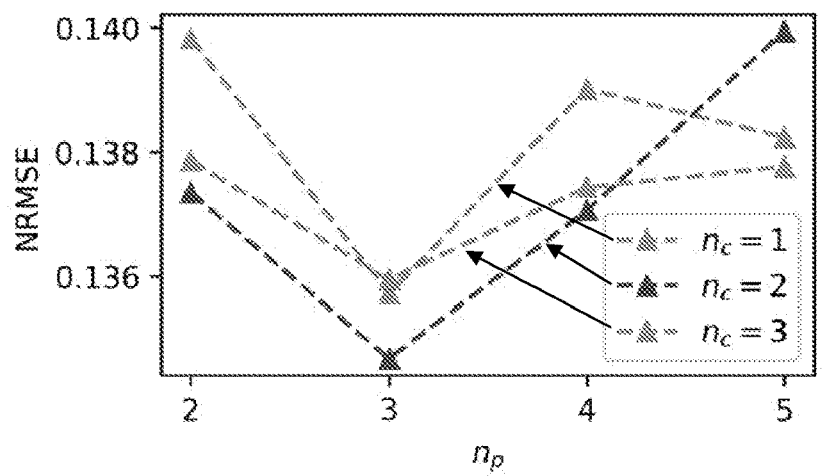
FIGS. 11A-11C show the performance of networks without different depth evaluated with average NRMSE, PSNR and SSIM over all the 9 subjects in a study with the current invention.
Figure 11B:
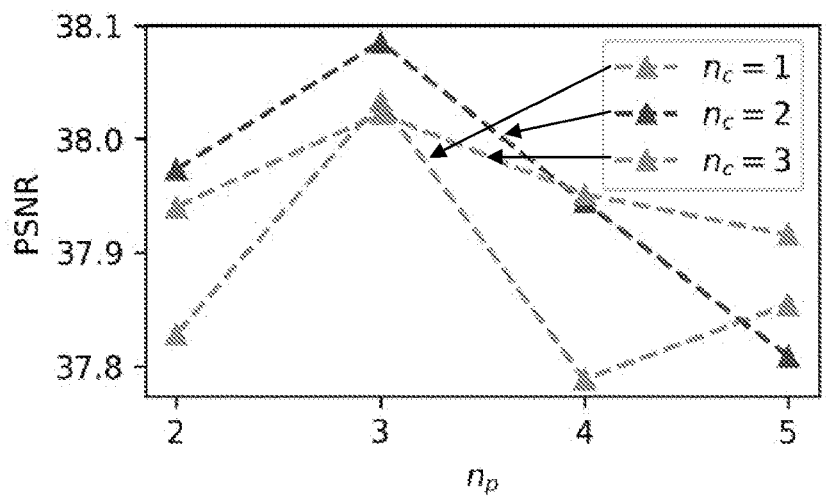
Figure 11C:
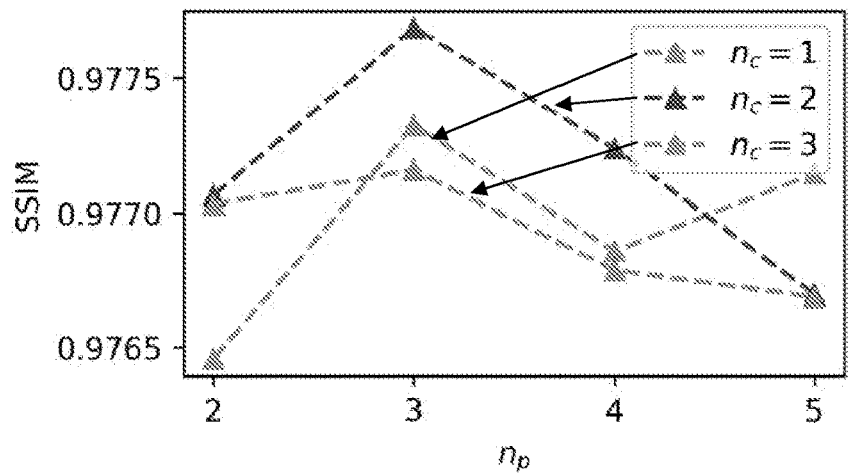

Regarding the depth of the network, to optimize network of the current invention, experiments are conducted to evaluate the impact of depth of the invention's model on the network performance. Two hyper-parameters are used to control the depth of this network, namely number of pooling layers (np) and number of convolutions between two poolings (nc). The strategy of grid search is adopted. In an example experiment, np varies from 2 to 5 while nc varies from 1 to 3. The results are shown in FIG. 11, which suggest that np=3 and nc=2 is the best architecture in this example.

A sample test is provided, where for SUV:

$$Mean(ROI) = \frac{\sum_{j \in ROI} I(j)}{N_{ROI}}$$

$$SD(ROI) = \sqrt{\frac{\sum_{j \in ROI}(I(j) - Mean(ROI))^2}{N_{ROI}}}$$

$$SN\ R(ROI) = \frac{Mean(ROI)}{SD(VOI)}$$

To access the perceptual image quality of resulting images an expert radiologist was invited to rate the images based on their quality and resolution. Each image was rated on a 1-5 scale (higher=better). Image ratings were dichotomized into 1-3 or 4-5, and the percentage of images rated 4-5 was calculated for each image type (II). Non-inferiority tests of synthesized vs high-dose images were performed by constructing the 95% confidence interval (III) for the difference in their proportions of high ratings and comparing the lower bound of the interval to a non-inferiority margin of −15 percentage points. This tested (with a significance level of 0.05) whether the proportion of high ratings for synthesized images was no more than 15 percentage points lower than that for high-dose images. Statistical analyses were done using Stata 15.1 (StataCorp LP, College Station, Tex.) and R version 3.3.1 (r-project.org) with version 1.3 of the Exact-CIdiff" package.

TABLE II

PERCENTAGE OF IMAGES RATED 4 OR 5 FOR EACH IMAGE TYPE

| Measure | | SD | ResUNet | ResUNet + MR | LD |
|---|---|---|---|---|---|
| Quality | | 100% | 60% | 90% | 0% |
|  | | (69-100%) | (26-88%) | (55-99%) | (0-31%) |
| Resolution | | 80% | 20% | 60% | 10% |
|  | | (44-97%) | (3-57%) | (26-88%) | (0-45%) |

TABLE III

CONFIDENCE INTERVALS FOR THE DIFFERENCE IN PROPORTIONS BETWEEN STANDARD-DOSE AND SYNTHESIZED

|  |  | ResUNet | ResUNet + MR |
|---|---|---|---|
| Quality | Difference | −40% | −10% |
|  | 95% CI | (−74%, 1%) | (−39%, 1%) |
| Resolution | Difference | −60% | −20% |
|  | 95% CI | (−88%, 14%) | (−56%, 14%) |

To study the effect to clinical diagnosis of the method according to the current invention, a segmentation test for lesion was also conducted. Seven out of eight subjects were included in this test, since no hot lesion was observed in the remaining subject. The contour of tumors were labeled by a radiologist on the standard dose images, deep learning (with and without MR) reconstructed images with DRF=100. The segmentation results on the standard dose images served as ground truth in this test. A re-test of the contours for the standard dose images was done by the same radiologist 3-weeks after the initial label. Several indexes are calculated, including DICE, precision, recall and area difference, which are listed in Table IV. Additionally, a T-test was conducted based on DICE coefficient, precision, recall and area difference.

TABLE IV

T-TEST RESULTS

| | case | F1(DICE) | Precision | Recall | Area Diff |
|---|---|---|---|---|---|
| Retest | 1 | 0.9465 | 0.9646 | 0.9291 | 14.00 |
| | 2 | 0.8907 | 0.9760 | 0.8191 | 32.00 |
| | 3 | 0.8649 | 0.9412 | 0.8000 | 12.00 |
| | 4 | 0.9326 | 0.9540 | 0.9121 | −4.00 |
| | 5 | 0.8413 | 0.9636 | 0.7465 | 16.00 |
| | 6 | 0.9249 | 0.9176 | 0.9323 | −4.00 |
| | 7 | 0.9352 | 0.9468 | 0.9238 | 24.00 |
| | Avg | 0.9067 | 0.9400 | 0.8815 | 9.50 |
| | Std | 0.0350 | 0.0359 | 0.0774 | 14.59 |
| DL + MR | 1 | 0.8504 | 0.7766 | 0.9396 | −80.00 |
| | 2 | 0.8423 | 0.7633 | 0.9397 | −46.00 |
| | 3 | 0.8027 | 0.8806 | 0.7375 | 13.00 |
| | 4 | 0.6203 | 0.6042 | 0.6374 | −5.00 |
| | 5 | 0.6329 | 0.5747 | 0.7042 | −16.00 |
| | 6 | 0.8387 | 0.8007 | 0.8805 | −25.00 |
| | 7 | 0.9078 | 0.9904 | 0.8379 | 95.00 |
| | Avg | 0.8200 | 0.7920 | 0.8564 | −16.75 |
| | Std | 0.0928 | 0.1003 | 0.1175 | 18.26 |
| T-test p-value | | 0.039 | 0.0066 | 0.560 | 0.023 |

Quantitative results in FIG. 4 and FIG. 5 show that the propose method demonstrated the best performance in all nine subjects in the data set, compared with other methods that were tested. From the visual results, it also suggests that the method of the current invention has the highest image quality. NLM produces patchy artifact in the image as shown in FIG. 6C. Both BM3D and AC-Net cannot fully remove the noise in low-dose image and tend to over-blur the image without recover important details, as illustrated in FIGS. 6D and 6E. The same conclusion can also be drawn from the error map in FIG. 8. In addition, the method of the current invention can achieve the best perceptual result in the region of GBM, as shown in FIG. 7.

In terms of computational costs, although deep learning requires a long time for training, their efficiency in inference can easily outperforms traditional methods due to efficient implementation with Tensorflow and parallelization on GPUs. Time consumptions of each method for a 256×256 image are listed in Table V. Compared with other methods, the solution by the current invention is not only more accurate but also more efficient.

TABLE V

TESTING TIME (PER Image) FOR EACH METHOD.

| Method | Average Speed/Image (ms) |
|---|---|
| NLM(CPU) | 1180 |
| NLM(GPU) | 63 |
| BM3D(CPU) | 680 |
| BM3D(GPU) | 232 |
| AC-Net(GPU) | 27 |
| Proposed(GPU) | 19 |

It is the encoder-decoder structure that enables the network to adopt more parameters and channels to extract higher level features while reducing computation time, compared with single-scale model used in AC-Net.

As the result shown in FIGS. 8A-8F, the model with both types of skip connections obviously achieves the best performance. However, for model with only one type of skip connection, their performances are close to that of the model without the skip connection, or even worse. These results indicate that these two kinds of connections are not independent.

A comparison of both quantitative and qualitative reconstruction using different options for combining multi-slice inputs is provided. Detailed structures in FIG. 9C are blurred during the denoising process, while they are preserved in FIGS. 9D-9F, which show the benefits from multi-slice inputs.

Since resolution of the 3D PET data along z axial direction is worse than within axial image, stacking a few slices along z axis can recover the 3D spatial relationship. Here it is shown that a significant performance improvement from the 2.5D slice with augmentation is provided by only using 3 slices, however the performance is not further improved by using more slices as inputs. This result is consistent with the assumption that the structural similarity of different slices persists until the relationship and redundancy one can leverage between slices vanish eventually due to distance.

As provided herein, a deep fully convolutional network was presented for ultra-low-dose PET reconstruction, where multiscale encoder-decoder architecture, concatenate connections and residual learning are adopted.

The results showed the method of the current invention has superior performance in reconstructing high-quality PET images and generating comparable quality as from normal-dose PET images. The method significantly reduces noise while robustly preserve resolution and detailed structures.

In addition, demonstrated herein is how different components of the method of the current invention contributes to the improved performance: the design of loss function, 2.5D multi-slice inputs as well as concatenating and residual skip connections, etc. Detailed quantitative and qualitative comparison proved the method of the current invention can better preserve structure and avoid hallucination due to noise and artifacts.

With extensive comparison, the method of the current invention achieves significantly better reconstruction compared with previous methods from ultra-low-dose PET data from 0:5% of the regular dose, potentially enabling safer and more efficient PET scans.

Figure 12:
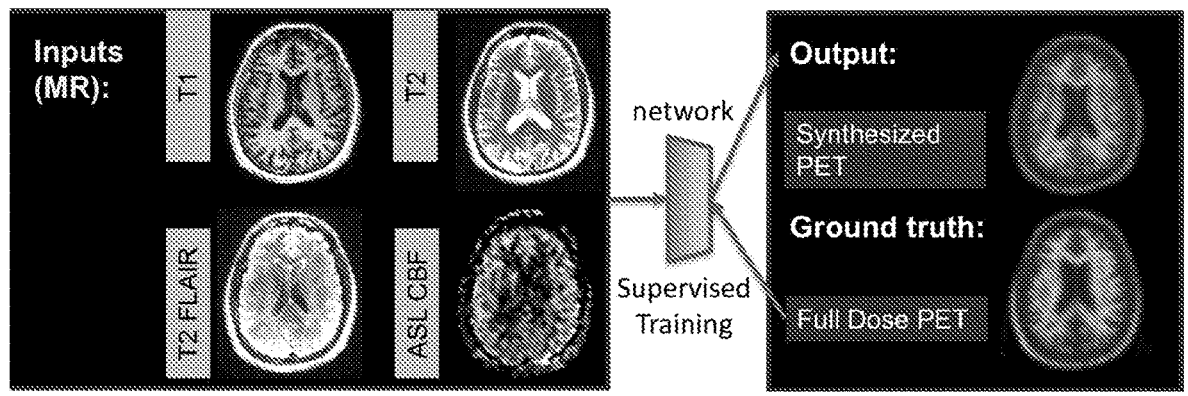
FIG. 12 shows an experimental result using the deep learning workflow for predicting PET, according to the current invention.

As stated above, MRI has great clinical values to distinguish soft-tissues without contrast or radiation. By using the hybrid-modality information from MRI and PET, the current invention provides a deep learning system and method to predict metabolic activity mapping (as measured in PET) from contrast-free multi-contrast MRI images. Demonstrated and validated below are clinical datasets for both FDG-PET/MRI and Amyloid-PET/MRI clinical datasets. This technique can be used for more efficient, low-cost, multi-tracer functional imaging using Deep Learning. For the method, simultaneous PET/MRI Datasets (FDG-PET/MRI and Amyloid-PET/MRI) were acquired in neuro exams using simultaneous time-of-flight enabled 3.0 Tesla PET/MRI system (Signa, GE Healthcare, Waukesha, Wis.). The datasets are collected on 10 Glioblastomas (GBM) patients for FDG-PET/MRI and another 20 subjects (include both healthy control and AD patients) for Amyloid-PET/MRI. Here, deep Learning models are shown in FIG. 12, used here was a subset of images acquired in contrast-free MRI scans, including ASL, FLAIR, T1w and T2w MR images, to predict the metabolic information as in PET image. By using ASL and other anatomical MRI scans as inputs, with normalized metabolic activities measured from PET as ground-truth reference, a U-Net deep network model was trained to output the approximated metabolic signals. Further, evaluation with 5-fold cross-validation was used to quantify the performance in which the model is trained on 80% subset of subjects and applied on the other 20% datasets. The performance was evaluated using quantitative similarity metrics: PSNR, SSIM and normalized Mutual Information (MI).

Table VI shows quantitative similarity metrics between the ground-truth metabolic activation originally measured using FDG-PET, with estimated metabolic map using the method and system of the current invention, and with all raw MRI images.

TABLE VI

| Similarity Metrics | DL Estimation | ASL | FLAIR | T1 | T2 |
|---|---|---|---|---|---|
| PSNR | 34.3 ± 1.5 | 23.5 ± 1.3 | 22.5 ± 0.9 | 20.3 ± 0.7 | 18.7 ± 0.4 |
| SSIM | 0.97 ± 0.01 | 0.78 ± 0.02 | 0.81 ± 0.01 | 0.81 ± 0.01 | 0.76 ± 0.01 |
| Mutual-Information | 0.86 ± 0.13 | 0.51 ± 0.07 | 0.50 ± 0.06 | 0.49 ± 0.05 | 0.47 ± 0.06 |

Figure 13:
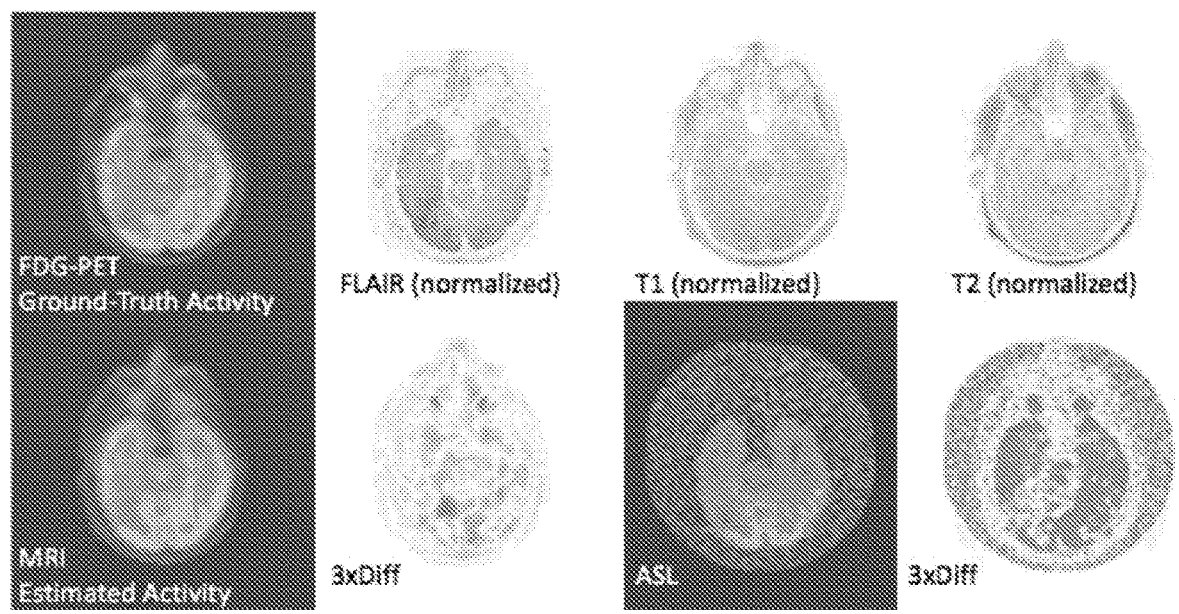
FIG. 13 shows a visualization of predicting FDG-PET, according to the current invention.

FIG. 13 shows visualized results of an axial slices with GBM cold-lesion and shows the proposed system and method of the current invention that can accurately predict the metabolic activation. On average, the estimated FDG-activation-liked metabolic achieves good approximation with 34.3±1.5 dB in PSNR, 0.97±0.01 in SSIM and 0.85±0.13 in Mutual Information. For comparison, the metrics from regression from ASL-MRI signal, which is the most similar MIll contrast to PET, is 23.5 dB for PSNR, 0.78 for SSIM and 0.51 for MI. Similar results are shown for using MIll to map the information as in Amyloid-PET. FIG. 13 shows example slices demonstrating accurate approximation for Amyloid-PET from MRI. With the system and method of the current invention, one can achieve over 10 dB gains in PSNR and more than 0.3 SSIM improvements.

Figure 14:
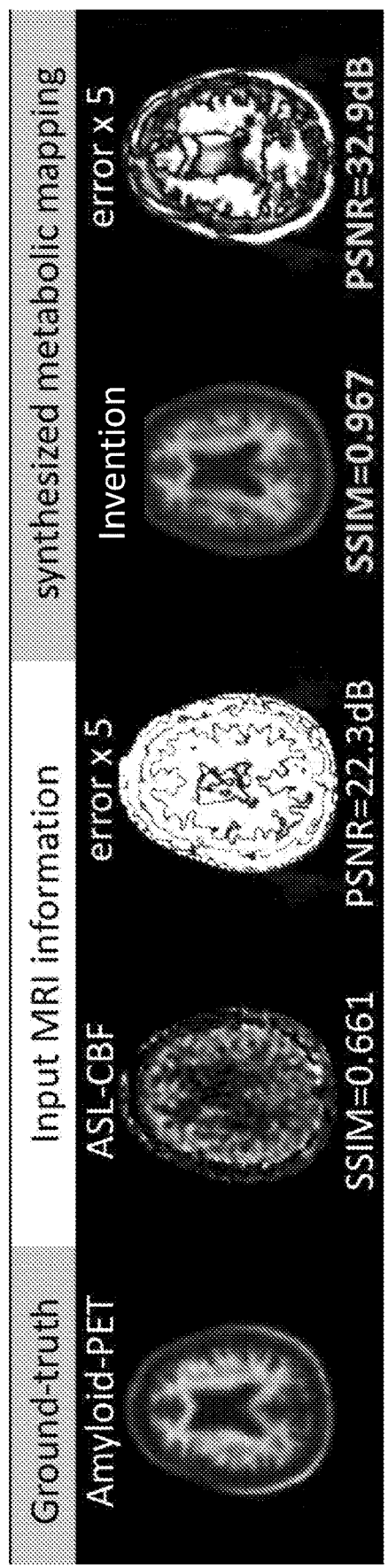
FIG. 14 shows a synthesized amyloid-PET from MRI, according to one embodiment of the invention.
Figure 15:
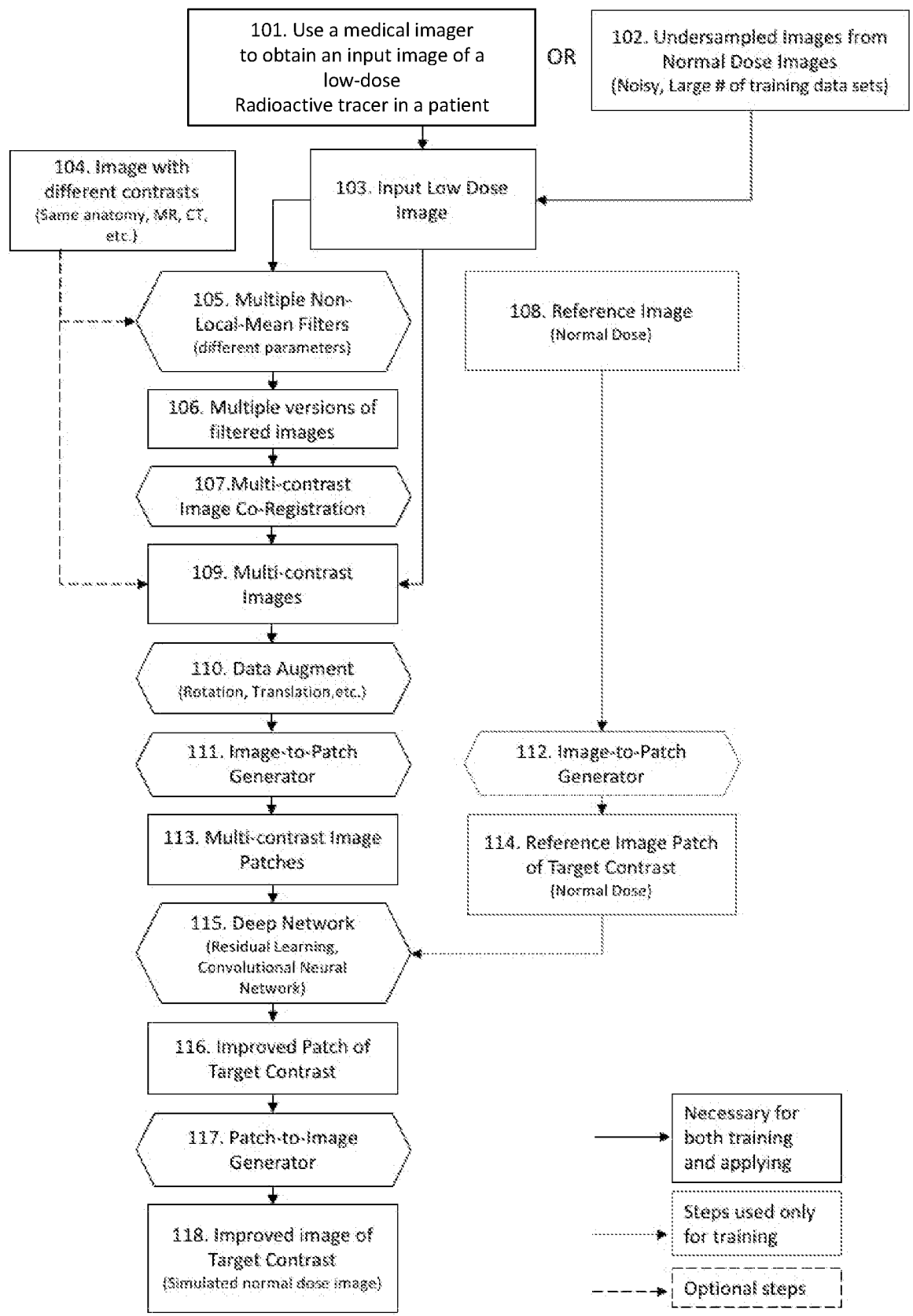
FIG. 15 shows a flow diagram of a process according to one embodiment of the invention.

FIG. 14 shows a synthesized amyloid-PET from MRI, according to one embodiment of the invention. FIG. 15 shows a flow diagram of a process according to one embodiment of the invention.

Using simultaneous PET/MRI, the invention is demonstrated to feasibly estimate multi-tracer metabolic biomarker from contrast-free MRI images. It can be used for more efficient, low-cost, multi-tracer functional imaging, exploring anatomy-function relationship, and improving the workflow.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

All such variations are considered to be within the scope and spirit of the present invention as defined by the following claims and their legal equivalents.

What is claimed:

1. A method of reducing radiotracer dose for radiology imaging modalities and nuclear medicine applications, comprising: using a convolutional network to generate a standard-dose nuclear medicine image from a low-dose nuclear medicine image, wherein said convolutional network comprises N convolution neural network (CNN) stages, wherein each said CNN stage comprises M convolution layers having K x K kernels, wherein said convolutional network further comprises an encoder-decoderstructure having symmetry concatenate connections between corresponding said CNN stages;

wherein said convolutional network implements downsampling using pooling and up-sampling using bilinear interpolation between said stages, wherein said convolutional network extracts multi-scale and high-level features from said low-dose image to simulate the standard-dose image; and wherein said convolutional network implements uses concatenate connections to preserve local information and resolution of said standard dose image, wherein said standard-dose image comprises a dose reduction factor (DRF) equal to 1 of a radio tracer in a patient, wherein said low-dose image comprises a DRF equal to at least4 of said radio tracer in said patient.

2. The method according to claim 1, wherein said DRF is in a range of 4 to 200.

3. The method according to claim 1, wherein said standard-dose nuclear medicine image is generated from said low-dose nuclear medicine image and corresponding multi-contrast MR images as multi-modality inputs.

4. The method according to claim 1, wherein said nuclear medicine image is generated using methods selected from the group consisting of CT, PET, PET/CT, PET/MIR, SPECT, and other nuclear medicine imaging methods.

5. The method according to claim 1, wherein a signal-to-noise-ratio (SNR) in said low-dose nuclear medicine image is increased using an encoder-decoder residual deep network with concatenate skip connections, wherein said skip connections comprise a residual connection from an input to an output of said method, or concatenating connections between corresponding encoder and decoder layers.

6. The method according to claim 1, wherein said low-dose nuclear medicine image further comprises a combination of multiple slices and multiple contrast images as input.

7. The method according to claim 6, wherein said combination of said multiple slices and said multiple contrast images are selected from the group consisting of T1w MR images, T2w MR images, FLAIR MR images, Diffusion MR images, Perfusion MRI images, susceptibility MR images, MR based Attenuation Correction Maps, MR water-fat images, CT images, and CT based Attenuation Correction Maps, wherein said Perfusion MRI images comprise Arterial Spin Labeling sequences.

8. The method according to claim 1 further comprising an algorithm to determine how many input slices and which input contrasts are contributing the most to the method, wherein said algorithm adaptively decides how many said input slices and said input contrasts to use.

9. The method according to claim 1, wherein mixed cost functions selected from the group consisting of L1/Mean-absolute-error, structural similarity loss, and adaptive trained loss are used, where said adaptive trained loss comprises generative adversarial network loss and perceptual loss function using network models.

10. A system of generating high-quality images for radiology imaging modalities and nuclear medicine applications from low-radiation-dose samples comprising:

a) using a medical imager for taking multiple slices of low-radiation-dose images, or low-radiation-dose images and multi-contrast images acquired together, as a stacking of multiple 2 dimensional images or 3 dimensional images as a system input;

b) applying a deep network-based regression task to said input images, wherein said deep network-based regression task comprises;

i. N convolution neural network (CNN) stages, wherein each said CNN stage comprises M convolution layers having K×K kernels, wherein said CNN comprises an encoder-decoder structure having symmetry concatenate connections between corresponding said CNN stages;

ii. an encoder-decoder residual deep network with concatenate skip connections, wherein said skip connections comprise a residual connection from an input image to an output image; and
iii. outputting radiology or nuclear medicine images having an image quality as a standard-radiation-dose image, wherein said image quality comprises a resolution, a contrast, and a signal-to-noise-ratio that are improved from low-radiation-dose inputs.

* * * * *